United States Patent [19]
Alberts et al.

[11] Patent Number: 5,135,935
[45] Date of Patent: Aug. 4, 1992

[54] SQUALENE SYNTHETASE INHIBITORS

[75] Inventors: Alfred W. Alberts, Princeton; Gregory D. Berger, Belle Meade; James D. Bergstrom, Neshanic Station, all of N.J.

[73] Assignee: Merck & Co., Inc., Rahway, N.J.

[21] Appl. No.: 701,922

[22] Filed: May 17, 1991

[51] Int. Cl.$^5$ .............................................. A61K 31/44
[52] U.S. Cl. .................................................... 514/305
[58] Field of Search ......................................... 514/305

[56]  References Cited
U.S. PATENT DOCUMENTS 4,806,564  2/1989  Chabala et al. ...................... 514/449
4,900,754  2/1990  Regan et al. ......................... 514/459

FOREIGN PATENT DOCUMENTS 0318860  6/1989  European Pat. Off. .

OTHER PUBLICATIONS

Ma et al. *PNAS* 83 8370–8374 (1986).
Swain et al., *J. Med. Chem. Soc.* 34 140–151 (1991).
Saunders et al., *J. Med. Chem.* 33 1128–1138 (1990).

*Primary Examiner*—Frederick E. Waddell
*Assistant Examiner*—Kimberly R. Jordan
*Attorney, Agent, or Firm*—Joseph F. DiPrima; William H. Nicholson; Melvin Winokur

[57]  ABSTRACT

Compounds of structural formula (I):

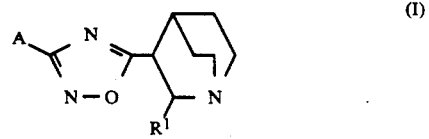

are squalene synthestase inhibitors useful in inhibiting the biosynthesis of cholesterol in the treatment of hypercholesterolemia and related disorders.

24 Claims, No Drawings

SQUALENE SYNTHETASE INHIBITORS

SUMMARY OF THE INVENTION

This invention relates to a method of inhibiting cholesterol biosynthesis comprising the administration to a subject in need of such treatment of a non-toxic therapeutically effective amount of a compound represented by structural formula (I):

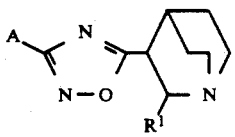
(I)

wherein A and $R^1$ are hereinafter defined, and pharmaceutically acceptable salts thereof. Compounds of formula (I) are squalene synthetase inhibitors.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective, but they must be consumed in large quantities, i.e., several grams at a time, and they are not very palatable.

MEVACOR® (lovastatin), now commercially available, is one of a group of very active antihypercholesterolemic agents that function by limiting cholesterol biosynthesis by inhibiting the enzyme, HMG-CoA reductase. These compounds inhibit early steps in cholesterol synthesis and may also inhibit the synthesis of other isoprenoids, such as dolichol, ubiquinone, and isopentenyl-t-RNA.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed compounds containing pyrophosphate or a pyrophosphate analog such as those described in P. Ortiz de Montellano et al., J. Med. Chem., 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl) phosphonates as inhibitors of squalene synthetase. Other squalene synthetase inhibitors include the recently discovered Zaragozic acids. However, a need still remains for a more effective squalene synthetase inhibitor, i.e., one that provides a greater antihypercholesteremic effect and exhibits a good safety profile.

The present invention provides nonphosphorus containing quinuclidinyl-oxadiazole inhibitors of squalene synthetase. These compounds are known to be useful for the treatment of psychotic disorders or as intermediates in the synthesis of psycho-active agents.

DETAILED DESCRIPTION OF THE INVENTION

The present invention is directed to a method of inhibiting cholesterol biosynthesis comprising the administration to a subject in need of such treatment of a non-toxic, therapeutically effective amount of a compound represented by structural formula (I)

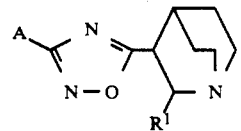
(I)

or a pharmaceutically acceptable salt thereof, wherein:
$R^1$ is hydrogen or $C_{1-3}$ alkoxy; and
A is 1) 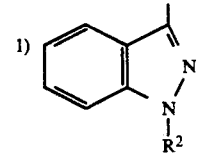

wherein $R^2$ is hydrogen or $C_{1-3}$ alkyl;

2) 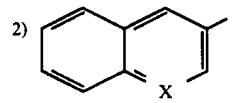

wherein X is —CH— or —N—;

3) 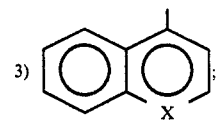

4) 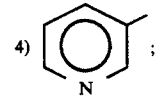

5) 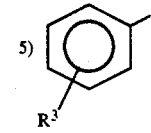

wherein $R^3$ is —H, —OH, —F, $C_{1-3}$ alkyl or $C_{1-3}$ alkoxy;

6) 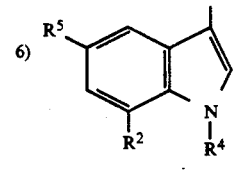

wherein:
$R^4$ is
  a) —H,
  b) $C_{1-3}$ alkyl, or
  c) $C_{2-3}$ alkenyl; and
$R^5$ is a) —H,
b) —F, —Cl, or —Br, or
c) $C_{1-3}$ alkyl;

7) 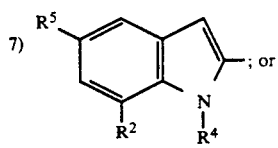; or

8) 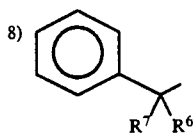

wherein $R^6$ and $R^7$ together represent =O, or $R^6$ and $R^7$ are independently selected from the group consisting of:
a) hydrogen,
b) hydroxyl,
c) $C_{1-3}$ alkyl,
d) $C_{2-3}$ alkenyl
e) 2-naphthyl,
f) phenyl
g) 4-substituted phenyl wherein the substituent is —F, —Cl, —Br, or hydroxyl, and
h) $C_{2-3}$ alkanoyloxy.

A preferred embodiment of the novel method of treatment of this invention comprises administration of the compound of Formula (I) wherein:
$R^1$ is hydrogen;
$R^2$ is —H, or —CH$_3$;
$R^3$ is —H, —OH, or —OCH$_3$;
$R^4$ is —H, —CH$_3$, or —CH$_2$—CH=CH$_2$;
$R^5$ is —H, —F, or —CH$_3$; and
$R^6$ and $R^7$ together represent =O or $R^6$ and $R^7$ are independently selected from hydrogen, hydroxyl, methyl, ethyl, ethenyl, 2-naphthyl, acetoxy, phenyl, and 4-substituted phenyl wherein the substituent is fluoro or hydroxyl.

An especially preferred embodiment of the novel method of treatment of this invention comprises administration of the compound of structural formula (I) which is:
1. 3-[3-(phenylmethyl)-1,2,4-oxadiazol-5-yl]-1-azabicyclo[2.2.2]octane;
2. 3-[3-(1-phenylethyl-1,2,4-oxadiazol-5-yl]-1-azabicyclo[2.2.2]octane;
3. 3-[3-(1-methyl-1H-indol-3-yl)-1,2,4-oxadiazol-5-yl]-1-azabicyclo[2.2.2]octane;
4. 3-[3-(5-fluoro-1-methyl-1H-indol-3-yl)-1,2,4-oxadiazol-5-yl]-1-azabicyclo[2.2.2]octane;
5. α-methyl-α-phenyl-5-(1-azabicyclo[2.2.2]oct-3-yl)-1,2,4-oxadiazole-3-methanol;
6. 3-[3-(1-acetoxy-1-phenylmethyl)-1,2,4-oxadiazol-5-yl]-quinuclidine;
7. α-phenyl-5-(1-azabicyclo[2.2.2]oct-3-yl)-1,2,4-oxadiazole-3-methanol;
8. 3-[3-(1-methyl-1H-indol-3-yl)-1,2,4-oxadiazol-5-yl]-1-azabicyclo[2.2.2]octane);
9. α-ethyl-α-phenyl-5-(1-azabicyclo[2.2.2]oct-3-yl)-1,2,4-oxadiazole-3-methanol;
10. α-ethenyl-α-phenyl-5-(1-azabicyclo[2.2.2]-oct-3-yl)-1,2,4-oxadiazole-3-methanol;
11. 3-[3-(diphenylmethyl)-1,2,4-oxadiazol-5-yl]-1-azabicyclo[2.2.2]octane;
12. α-(4-fluorophenyl)-α-phenyl-5-(1-azabicyclo[2.2.2]oct-3-yl)-1,2,4-oxadiazole-3-methanol;
13. α-(4-methoxyphenyl)-α-phenyl-5-(1-azabicyclo[2.2.2]oct-3-yl)-1,2,4-oxadiazole-3-methanol;
14. α-2-naphthalenyl-α-phenyl-5-(1-azabicyclo[2.2.2]oct-3-yl)-1,2,4-oxadiazole-3-methanol;
15. 3-[3-(1-methyl-1H-indol-2-yl)-1,2,4-oxadiazol-5-yl]-1-azabicyclo[2.2.2]octane;
16. 2-methoxy-3-[3-(1-methyl-1H-indol-3-yl)-1,2,4-oxadiazol-5-yl]-1-azabicyclo[2.2.2]octane;
17. 3-[3-(1H-indazol-3-yl)-1,2,4-oxadiazol-5-yl]-1-azabicyclo[2.2.2]octane;
18. 3-[3-(1,7-dimethyl-1H-indol-3-yl)-1,2,4-oxadiazol-5-yl]-1-azabicyclo[2.2.2]octane;
19. 3-[3-(1,5-dimethyl-1H-indol-3-yl)-1,2,4-oxadiazol-5-yl]-1-azabicyclo[2.2.2]octane;
20. 3-[3-(1H-indol-3-yl)-1,2,4-oxadiazol-5-yl]-1-azabicyclo[2.2.2]octane;
21. (+)-3-[3-(1-methyl-1H-indol-3-yl)-1,2,4-oxadi-azol-5-yl]-1-azabicyclo[2.2.2]octane;
22. (−)-3-[3-(1-methyl-1H-indol-3-yl)-1,2,4-oxadiazol-5-yl]-1-azabicyclo[2.2.2]octane;
23. 3-[3-(2-naphthalenyl)-1,2,4-oxadiazol-5-yl]-1-azabicyclo[2.2.2]octane;
24. 3-[3-phenyl-1,2,4-oxadiazol-5-yl]-1-azabicyclo[2.2.2]octane;
25. 3-[3-(1-(2-propenyl)-1H-indol-3-yl]-1,2,4-oxadiazol-5-yl]-1-azabicyclo[2.2.2]octane;
26. 3-[3-(3-pyridinyl)-1,2,4-oxadiazol-5-yl]-1-azabicyclo[2.2.2]octane;
27. 3-[3-(1-naphthalenyl)-1,2,4-oxadiazol-5-yl]-1-azabicyclo[2.2.2]octane;
28. 3-[3-(3-methoxyphenyl)-1,2,4-oxadiazol-5-yl]-1-azabicyclo[2.2.2]octane;
29. 3-[3-(2-methoxyphenyl)-1,2,4-oxadiazol-5-yl]-1-azabicyclo[2.2.2]octane;
30. 3-[3-(4-methoxyphenyl)-1,2,4-oxadiazol-5-yl]-1-azabicyclo[2.2.2]octane;
31. 2-[5-(1-azabicyclo[2.2.2]oct-3-yl)-1,2,4-oxadiazol-5-yl]-phenol;
32. 3-[5-(1-azabicyclo[2.2.2]oct-3-yl)-1,2,4-oxadiazol-5-yl]-phenol;
33. 4-[5-(1-azabicyclo[2.2.2]oct-3-yl)-1,2,4-oxadiazol-5-yl]-phenol;
34. 3-[3-(1,1-diphenyl-1-hydroxymethyl)-1,2,4-oxadiazol-5-yl]-quinuclidine;
35. 3-[3-(1H-indol-3-yl)-1,2,4-oxadiazol-5-yl]-1-azabicyclo[2.2.2]octane;
36. 3-[3-(3-quinolyl)-1,2,4-oxadiazol-5-yl]-1-azabicyclo[2.2.2]octane; or
37. 3-(3-benzoyl-1,2,4-oxadiazol-5-yl)quinuclidine;
or a pharmaceutically acceptable salt thereof.

Most of the compounds of this invention have one asymmetric center and often more than one, and can therefore exist both as enantiomers and as diastereoisomers. In particular, those compounds possessing an unsymmetrical quinuclidine ring system with more than one substituent may exist as exo and endo diastereomers. It is to be understood that the invention covers all such isomers and mixtures thereof.

The pharmaceutically acceptable salts of the compounds of this invention include those formed from anions such as fluoride, chloride, bromide, iodide, oxalate, citrate, acetate, ascorbate, fumarate, malate, succinate, tartarate, carbonate, phosphate, and the like. Alternatively, these compounds may be administered as the quinuclidinium borohydride. Especially preferred are the chloride, citrate and oxalate salts.

Specifically, the compounds of this invention are useful as antihypercholesterolemic agents for the treatment of arteriosclerosis, hyperlipidemia, familial hypercholesterolemia, and like disease in humans. They may be administered orally or parenterally in the form of a capsule, a tablet, an injectable preparation or the like. It is usually desirable to use the oral route.

For preparing solid compositions such as tablets, the principal active ingredient is mixed with a pharmaceutical carrier, e.g., conventional tabletting ingredients such as corn starch, lactose, sucrose, sorbitol, talc, stearic acid, magnesium stearate, dicalcium phosphate or gums, and other pharmaceutical diluents, such as water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 1 to about 400 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups and flavored emulsions with edible oils such as cottonseed oil, sesame oil, coconut oil, and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone and gelatin.

Doses may be varied, depending on age, severity, body weight and other conditions, but the daily dosage for adults is within a range of about 10 mg to 400 mg, preferably 20 to 200 mg, which may be given in one to four divided doses. Higher doses may be favorably employed as required.

The compounds of this invention may also be administered in combination with other cholesterol-lowering agents such as those which inhibit another enzyme in the biosynthetic pathway in the synthesis of cholesterol. Examples of such agents would include but are not limited to HMG-CoA reductase inhibitors, HMG-CoA synthase inhibitors, and squalene epoxidase inhibitors. Illustrative of such inhibitors are lovastatin, simvastatin, pravastatin and fluvastatin. Other cholesterol lowering agents that may be administered include niacin, probucol, the fibric acids, clofibrate and gemfibrozil, and LDL-receptor gene inducers. Representative of such combinations are those containing about 10–400 mg of a compound of formula (I) in combination with about 20–100 mg of an HMG-CoA reductase inhibitor or 250–1000 mg of probucol or 600–1200 mg of gemfibrozil or 1–2 g of clofibrate, or 3–6 g of niacin, or 20–300 mg of an LDL-receptor gene inducer.

The compounds of this invention may also be co-administered with pharmaceutically acceptable non-toxic cationic polymers capable of binding bile acids in a non-resorbable form in the gastrointestinal tract. Examples of such polymers include cholestyramine, colestipol and poly[methyl-(3-trimethyl)aminopropyl]iminotrimethylene dihalide. The relative amounts for co-administration of the compounds of this invention and these polymers is between 1:100 and 1:15,000 (w/w).

PREPARATION OF COMPOUNDS

The syntheses of the compounds of Formula (I) have been described in the following publications: EP 0 323 864 A2; U.S. Pat. No. 4,952,587; J. Med. Chem., 33, 1128 (1990); and J. Med. Chem., 34, 140 (1991). The syntheses of Compounds 1, 2, 5, 6, 7, 9, 10, 11, 12, 13, 14, 24, 28, 29, 30, 31, 32, 33, 34, and 37 are described in EP 0 323 864 A2. The syntheses of Compounds 3, 4, 8, 15, 16, 17, 18, 19, 20, 21, 22, 25 and 35 are described in U.S. Pat. No. 4,952,587. The syntheses of Compounds 23, 26, 27, and 36 are described in J. Med. Chem., 34, 140 (1991).

SQUALENE SYNTHETASE ACTIVITY

The intrinsic squalene synthetase inhibitory activity of representative compounds of this invention was measured by the standard in vitro protocol described below:

Preparation of Microsomes

Male, Charles River CD rats (120 to 150 g) were fed a diet containing 0.1% lovastatin for 4 days. The livers from these rats were homogenized in 5 volumes (mL/g) of ice cold 50 mM HEPES (4-(2-hydroxyethyl)-1-piperazine-ethanesulfonic acid), 5 mM EDTA (ethylenediaminetetraacetic acid) pH 7.5 with a Potter-Elvehjem type tissue grinder. The homogenate was centrifuged twice at $20,000 \times g$ for 15 minutes at 4° C., discarding the pellet each time. The supernatant was then centrifuged at $100,000 \times g$ for 1 hour at 4° C. The resulting microsomal pellet was resuspended in a volume of the above homogenizing buffer equal to one-fifth the volume of the original homogenate. This microsomal preparation has a protein concentration of about 7 mg/mL. The microsomal suspensions were stored in aliquots at $-70°$ C. Squalene synthetase activity in these aliquots is stable for at least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1 $\mu$mole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 $\mu$M leupeptin, 0.005% phenylmethyl sulfonyl fluoride pH 7.0 containing 0.1 trypsin inhibitor units of aprotinin/mL. The homogenate was centrifuged at 20,000×g for 20 minutes. The supernatant was adjusted to pH 5.5. with 6N HOAc and centrifuged at 100,000×g for 1 hour. This supernatant was adjusted to pH 7.0 with 3N KOH and a 35–60% ammonium sulfate fraction taken. The 60% pellet was redissolved in 60 mL of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 mL of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 mL of 10 mM Tris, 10 mM β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/mL with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

Enzymatic Synthesis of [4-$^{14}$C]farnesyl-pyrophosphate

The solvent (ethanol: 0.15N NH$_4$OH, 1:1) was removed from 55 μCi of [4-$^{14}$C]isopentenyl pyrophosphate(47.9 μCi/μmole) by rotary evaporation. Six hundred microliters of 100 mM Tris, 10 mM MgCl$_2$, 4 mM dithiothreitol pH 7.5 was added and the solution was transferred to a 1.5 ml Eppendorf centrifuge tube. Geranyl-pyrophosphate, 250 μL of a 20 mM solution, and 50 μL of the ammonium sulfate suspension of prenyl transferase were added to initiate the reaction. This incubation contained 5 μmoles of geranyl pyrophosphate, 1.15 μmoles of isopentenyl pyrophosphate, 6 μmoles of MgCl$_2$ of 0.18 units of prenyl transferase in a volume of 900 μL. The incubation was conducted at 37° C. During the incubation, the mix turned cloudy white as the newly formed magnesium complex of farnesyl pyrophosphate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 mL of 50 mM HEPES, 5 mM EDTA, pH 7.5. The yield was 50.7 μCi (92%) of [4-$^{14}$C]farnesyl pyrophosphate. The [4-$^{14}$C]farnesyl pyrophosphate was stored in aliquots at −70° C.

Squalene Synthetase Assay

Reactions were performed in 16×125 mm screw cap test tubes. A batch assay mix was prepared from the following solution:

| | μL per assay | volume for 50 assays |
|---|---|---|
| 1. 250 mM Hepes pH 7.5 | 40 | 2000 |
| 2. KF 110 mM | 20 | 1000 |
| 3. MgCl$_2$ 55 mM | 20 | 1000 |
| 4. Dithiothreitol 30 mM | 20 | 1000 |
| 5. NADPH 10 mM (made fresh) | 20 | 1000 |
| 6. [4-$^{14}$C]farnesyl-pyrophosphate 47.9 μCi/μmole, and 0.00479 μCi/6.0 μL | 6.0 | 300 |
| 7. 5 mM Na$_4$ pyrophosphate pH 7.5 with HCl | 40 or 0 | 2000 or 0 |
| 8. H$_2$O | 8 or 48 | 400 or 2400 |

If the assay was to be run in the presence of pyrophosphate, 40 μL of the 5 mM pyrophosphate solution and 8 μL of H$_2$O were added. If it was to be run without pyrophosphate, no pyrophosphate was added, and 48 μL of H$_2$O was added.

This assay mix was degassed under a vacuum and flushed with N$_2$. Solutions of the squalene synthetase inhibitors were prepared either in DMSO or MeOH and a 1:150 dilution of the microsomal protein was made with the original homogenizing buffer. For each reaction, 187 μL of the assay mix was taken with 3 μL of an inhibitor solution (DMSO or MeOH in the controls), warmed to 30° C. in a water bath and then the reaction was initiated by the addition of 10 μL of the 1:150 dilution of microsomal protein (0.5 μg protein total in the assay). The reactions were stopped after 20 minutes by the addition of 100 μL of a 1:1 mix of 40% KOH with 95% EtOH. The stopped mix was heated at 65° C. for 30 minutes, cooled, 10 mL of heptane was added and the mix was vortexed. Two g of activated alumina was then added, the mix vortexed again, the alumina allowed to settle and 5 mL of the heptane layer was removed. Ten mL of scintillation fluid was added to the heptane solution and radioactivity was determined by liquid scintillation counting.

Percent inhibition was calculated by the formula:

$$1 - \frac{[\text{Sample} - \text{Blank}]}{[\text{Control} - \text{Blank}]} \times 100$$

IC$_{50}$ values were determined by plotting the log of the concentration of the test compound versus the percentage inhibition. The IC$_{50}$ is the concentration of inhibitor that gives 50% inhibition as determined from these plots.

The following data and pharmaceutical formulation illustrate the activity and pharmaceutical formulations of the compounds of formula (I) and, as such, are not to be considered as limiting the invention set forth in the claims appended hereto.

Representative of the intrinsic squalene synthetase inhibitory activities of the compounds of this invention are the IC$_{50}$ data tabulated below.

TABLE I

IC$_{50}$'s for Squalene Synthetase Inhibition in Presence of 1 mM PPi

| Compound | Salt Form | Squalene Synthetase IC$_{50}$ (nM) |
|---|---|---|
| Compound 1 | oxalate | 409 |
| Compound 2 | oxalate | 43 |
| Compound 3 | oxalate | 28 |
| Compound 4 | oxalate | 19 |
| Compound 15 | oxalate | 20 |
| Compound 19 | oxalate | 58 |
| Compound 24 | oxalate | 43 |
| Compound 26 | oxalate | 660 |
| Compound 27 | oxalate | 11 |
| Compound 28 | hydrochloride | 31 |
| Compound 29 | hydrochloride | 250 |

TABLE I-continued

| IC$_{50}$'s for Squalene Synthetase Inhibition in Presence of 1 mM PPi | | |
|---|---|---|
| Compound | Salt Form | Squalene Synthetase IC$_{50}$ (nM) |
| Compound 35 | oxalate | 23 |
| Compound 36 | oxalate | 42 |

Representative of the squalene synthetase inhibitory activities of the compounds of this invention in the absence of pyrophosphate are the IC$_{50}$ data tabulated below.

TABLE II

| IC$_{50}$'s for Squalene Synthetase Inhibition in Absence of PPi | | |
|---|---|---|
| Compound | Salt Form | Squalene Synthetase IC$_{50}$ (nM) |
| Compound 3 | oxalate | 1600 |
| Compound 4 | oxalate | 1900 |
| Compound 15 | oxalate | 1100 |
| Compound 26 | oxalate | >10,000 |
| Compound 27 | oxalate | 2300 |
| Compound 28 | hydrochloride | 2800 |
| Compound 29 | hydrochloride | 14,000 |
| Compound 35 | oxalate | 1900 |

Representative of the squalene synthetase inhibitory activities of the compounds of this invention in the presence of pyrophosphate are the percent inhibition data tabulated below.

TABLE III

| Percent Inhibition of Squalene Synthetase in Presence of 1 mM PPi | | | |
|---|---|---|---|
| Compound | Salt Form | Conc. (μg/mL) | % Inhibition |
| Compound 1 | oxalate | 0.3 | 90% |
| Compound 4 | oxalate | 0.3 | 97% |
| Compound 6 | oxalate | 0.3 | 70% |
| Compound 7 | oxalate | 0.3 | 49% |
| Compound 19 | oxalate | 0.3 | 96% |
| Compound 24 | oxalate | 0.3 | 98% |
| Compound 27 | oxalate | 0.3 | 99% |
| Compound 28 | hydrochloride | 0.3 | 99% |
| Compound 30 | hydrochloride | 0.3 | 99% |
| Compound 31 | hydrochloride | 0.3 | 90% |
| Compound 32 | hydrochloride | 0.3 | 92% |
| Compound 33 | hydrochloride | 0.3 | 84% |
| Compound 34 | oxalate | 0.3 | 60% |
| Compound 35 | oxalate | 0.3 | 98% |
| Compound 36 | oxalate | 0.3 | 97% |
| Compound 37 | oxalate | 0.3 | 64% |

EXAMPLE

Tablets containing 10, 25, 50, 100 and 200 mg, respectively, of the active compound are prepared as illustrated below:

Table for doses containing from 10 to 50 mg of the active compound.

| | Amount-mg | | |
|---|---|---|---|
| Active Compound | 10.0 | 25.0 | 50.0 |
| Microcrystalline Cellulose | 32.75 | 37.25 | 100.0 |
| Modified Food Corn Starch | 32.75 | 37.25 | 4.25 |
| Magnesium Stearate | 0.50 | 0.50 | 0.75 |

Table for doses containing from 50 to 200 mg of the active compound.

| | Amount-mg | | |
|---|---|---|---|
| Active Compound | 100.0 | 200.0 | 400.0 |
| Microcrystalline Cellulose | 200.0 | 400.0 | 800.0 |
| Modified Food Corn Starch | 8.5 | 17.0 | 34.0 |
| Magnesium Stearate | 1.5 | 3.0 | 6.0 |

All of the active compound, cellulose, and a portion of the corn starch are mixed and granulated to a 10% corn starch paste. The resulting granulation is sieved, dried, and blended with the remainder of the corn starch and the magnesium stearate. The resulting granulation is then compressed into tablets containing 10 mg, 25 mg, 50 mg, 100 mg, 200 mg and 400 mg of the active ingredient per tablet.

What is claimed is:

1. A method of inhibiting squalene synthetase comprising administration to a human in need of such treatment of 10 to 400 mg per day of a squalene synthetase inhibitor of formula (I):

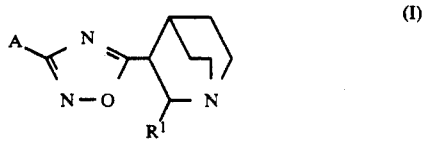

or a pharmaceutically acceptable salt thereof, wherein:
R$^1$ is hydrogen or C$_{1-3}$ alkoxy; and
A is 1) 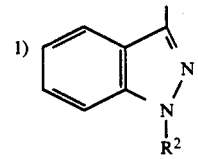

wherein R$^2$ is hydrogen or C$_{1-3}$ alkyl;

2) 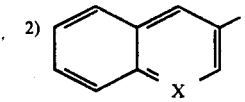

wherein X is —CH— or —N—;

3) 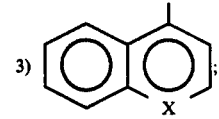

4) 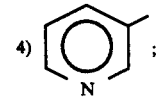

5) 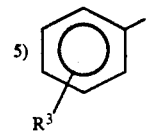

wherein R³ is —H, —OH, —F, C₁₋₃ alkyl or C₁₋₃ alkoxy;

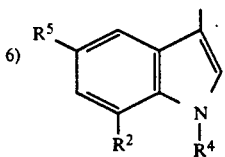

wherein:
R⁴ is
a) —H,
b) C₁₋₃ alkyl, or
c) C₂₋₃ alkenyl; and
R⁵ is
a) —H,
b) —F, —Cl, or —Br, or
c) C₁₋₃ alkyl;

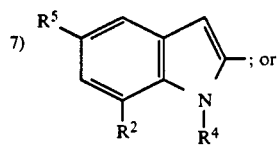

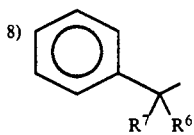

wherein R⁶ and R⁷ together represent =O, or R⁶ and R⁷ are independently selected from the group consisting of:
a) hydrogen,
b) hydroxyl,
c) C₁₋₃ alkyl,
d) C₂₋₃ alkenyl,
e) 2-naphthyl,
f) phenyl,
g) 4-substituted phenyl wherein the substituent is —F, —Cl, —Br, or hydroxyl, and
h) C₂₋₃ alkanoyloxy.

2. The method of claim 1 wherein:
R¹ is hydrogen;
R² is —H, or —CH₃;
R³ is —H, —OH, or —OCH₃;
R⁴ is —H, —CH₃, or —CH₂—CH=CH₂;
R⁵ is hydrogen, fluorine, or methyl; and
R⁶ and R⁷ together represent =O, or R⁶ and R⁷ are independently selected from hydrogen, hydroxyl, methyl, ethyl, ethenyl, 2-naphthyl, acetoxy, phenyl, and 4-substituted phenyl wherein the substituent is fluoro or hydroxyl.

3. The method of claim 1 wherein the squalene synthetase inhibitor is:
a) 3-[3-(phenylmethyl)-1,2,4-oxadiazol-5-yl]-1-azabicyclo[2.2.2]octane;
b) 3-[3-(1-phenylethyl)-1,2,4-oxadiazol-5-yl]-1-azabicyclo[2.2.2]octane;
c) 3-[3-(1-methyl-1H-indol-3-yl)-1,2,4-oxadiazol-5-yl]-1-azabicyclo[2.2.2]octane;
d) 3-[3-(5-fluoro-1-methyl-1H-indol-3-yl)-1,2,4-oxadiazol-5-yl]-1-azabicyclo[2.2.2]octane;

e) α-methyl-α-phenyl-5-(1-azabicyclo[2.2.2]-oct-3-yl)-1,2,4-oxadiazole-3-methanol;
f) 3-[3-(1-acetoxy-1-phenylmethyl)-1,2,4-oxadia-zol-5-yl]-quinuclidine;
g) α-phenyl-5-(1-azabicyclo[2.2.2]oct-3-yl)-1,2,4-oxadiazole-3-methanol;
h) 3-[3-(1-methyl-1H-indol-3-yl)-1,2,4-oxadiazol-5-yl]-1-azabicyclo[2.2.2]octane)boron;
i) α-ethyl-α-phenyl-5-(1-azabicyclo[2.2.2]oct-3-yl)-1,2,4-oxadiazole-3-methanol;
j) α-ethenyl-α-phenyl-5-(1-azabicyclo[2.2.2]oct-3-yl)-1,2,4-oxadiazole-3-methanol;
k) 3-[3-(diphenylmethyl)-1,2,4-oxadiazol-5-yl]-1-azabicyclo[2.2.2]octane;
l) α-(4-fluorophenyl)-α-phenyl-5-(1-azabicyclo[2.2.2]oct-3-yl)-1,2,4-oxadiazole-3-methanol;
m) α-(4-methoxyphenyl)-α-phenyl-5-(1-azabicyclo[2.2.2]oct-3-yl)-1,2,4-oxadiazole-3-methanol;
n) α-2-naphthalenyl-α-phenyl-5-(1-azabicyclo[2.2.2]oct-3-yl)-1,2,4-oxadiazole-3-methanol;
o) 3-[3-(1-methyl-1H-indol-2-yl)-1,2,4-oxadiazol-5-yl]-1-azabicyclo[2.2.2]octane;
p) 2-methoxy-3-[3-(1-methyl-1H-indol-3-yl)-1,2,4-oxadiazol-5-yl]-1-azabicyclo[2.2.2]octane;
q) 3-[3-(1H-indazol-3-yl)-1,2,4-oxadiazol-5-yl]-1-azabicyclo[2.2.2]octane;
r) 3-[3-(1,7-dimethyl-1H-indol-3-yl)-1,2,4-oxadiazol-5-yl]-1-azabicyclo[2.2.2]octane;
s) 3-[3-(1,5-dimethyl-1H-indol-3-yl)-1,2,4-oxadiazol-5-yl]-1-azabicyclo[2.2.2]octane;
t) 3-[3-(1H-indol-3-yl)-1,2,4-oxadizol-5-yl]-1-azabicyclo[2.2.2]octane;
u) (+)-3-[3-(1-methyl-1H-indol-3-yl)-1,2,4-oxadi-azol-5-yl]-1-azabicyclo[2.2.2]octane;
v) (−)-3-[3-(1-methyl-1H-indol-3-yl)-1,2,4-oxadiazol-5-yl]-1-azabicyclo[2.2.2]octane;
w) 3-[3-(2-naphthalenyl)-1,2,4-oxadiazol-5-yl]-1-azabicyclo[2.2.2]octane;
x) 3-[3-phenyl-1,2,4-oxadiazol-5-yl]-1-azabicyclo[2.2.2]octane;
y) 3-[3-(1-(2-propenyl)-1H-indol-3-yl]-1,2,4-oxadiazol-5-yl)-1-azabicyclo[2.2.2]octane;
z) 3-[3-(3-pyridinyl)-1,2,4-oxadiazol-5-yl]-1-azabicyclo[2.2.2]octane;
aa) 3-[3-(1-naphthalenyl)-1,2,4-oxadiazol-5-yl]-1-azabicyclo[2.2.2]octane;
bb) 3-[3-(3-methoxyphenyl)-1,2,4-oxadiazol-5-yl]-1-azabicyclo[2.2.2]octane;
cc) 3-[3-(2-methoxyphenyl)-1,2,4-oxadiazol-5-yl]-1-azabicyclo[2.2.2]octane;
dd) 3-[3-(4-methoxyphenyl)-1,2,4-oxadiazol-5-yl]-1-azabicyclo[2.2.2]octane;
ee) 2-[5-(1-azabicyclo[2.2.2]oct-3-yl)-1,2,4-oxadiazol-5-yl]-phenol;
ff) 3-[5-(1-azabicyclo[2.2.2]oct-3-yl)-1,2,4-oxadiazol-5-yl]-phenol;
gg) 4-[5-(1-azabicyclo[2.2.2]oct-3-yl)-1,2,4-oxadiazol-5-yl]-phenol;
hh) 3-[3-(1,1-diphenyl-1-hydroxymethyl)-1,2,4-oxadiazol-5-yl]-quinuclidine;
ii) 3-[3-(1H-indol-3-yl)-1,2,4-oxadiazol-5-yl]-1-azabicyclo[2.2.2]octane;
jj) 3-[3-(3-quinolyl)-1,2,4-oxadiazol-5-yl]-1-azabicyclo[2.2.2]octane; or
kk) 3-(3-benzoyl-1,2,4-oxadiazol-5-yl)quinuclidine;
or a pharmaceutically acceptable salt thereof.

4. A method of treating hypercholesterolemia comprising administration to a subject in need of such treatment of 10 to 400 mg per day of a squalene synthetase inhibitor of claim 1.

5. A method of treating hypercholesterolemia comprising administration to a subject in need of such treatment of 10 to 400 mg per day of a squalene synthetase inhibitor of claim 2.

6. A method of treating hypercholesterolemia comprising administration to a subject in need of such treatment of 10 to 400 mg per day of a squalene synthetase inhibitor of claim 3.

7. The method of claim 1, wherein the amount of the squalene synthetase inhibitor administered per day is from 20 to 200 mg.

8. The method of claim 2, wherein the amount of the squalene synthetase inhibitor administered per day is from 20 to 200 mg.

9. The method of claim 3, wherein the amount of the squalene synthetase inhibitor administered per day is from 20 to 200 mg.

10. The method of claim 4, wherein the amount of the squalene synthetase inhibitor administered per day is from 20 to 200 mg.

11. The method of claim 5, wherein the amount of the squalene synthetase inhibitor administered per day is from 20 to 200 mg.

12. The method of claim 6, wherein the amount of the squalene synthetase inhibitor administered per day is from 20 to 200 mg.

13. The method of claim 1 wherein the compound of formula (I) is administered as the hydrochloride, oxalate or citrate salt.

14. The method of claim 2 wherein the compound of formula (I) is administered as the hydrochloride, oxalate or citrate salt.

15. The method of claim 3 wherein the compound of formula (I) is administered as the hydrochloride, oxalate or citrate salt.

16. The method of claim 4 wherein the compound of formula (I) is administered as the hydrochloride, oxalate or citrate salt.

17. The method of claim 5 wherein the compound of formula (I) is administered as the hydrochloride, oxalate or citrate salt.

18. The method of claim 6 wherein the compound of formula (I) is administered as the hydrochloride, oxalate or citrate salt.

19. A pharmaceutical composition comprising 1 to 400 mg of a compound of claim 1 in combination with a pharmaceutically acceptable nontoxic cationic polymer capable of binding bile acids in a non-resorbable form in the gastrointestinal tract and a pharmaceutically acceptable carrier.

20. A pharmaceutical composition comprising 1 to 400 mg of a compound of claim 1 in combination with a nontoxic therapeutically effective amount of a cholesterol lowering agent selected from the group consisting of:

(a) HMG-CoA reductase inhibitor;
(b) HMG-CoA synthase inhibitor;
(c) Squalene epoxidase inhibitor;
(d) Probucol;
(e) Niacin;
(f) Gemfibrozil;
(g) Clofibrate; and
(h) LDL-receptor gene inducer.

21. A pharmaceutical composition comprising 1 to 400 mg of a compound of claim 1 and a nontoxic therapeutically effective amount of an HMG-CoA reductase inhibitor.

22. A composition of claim 21 wherein the HMG-CoA reductase inhibitor is selected from lovastatin, simvastatin, pravastatin and fluvastatin.

23. A pharmaceutical composition comprising 1 to 400 mg of a compound of claim 3 in combination with a pharmaceutically acceptable nontoxic cationic polymer capable of binding bile acids in a non-resorbable form in the gastrointestinal tract and a pharmaceutically acceptable carrier.

24. A pharmaceutical composition comprising 1 to 400 mg of a compound of claim 3 in combination with a nontoxic therapeutically effective amount of a cholesterol lowering agent selected from the group consisting of:

(a) HMG-CoA reductase inhibitor;
(b) HMG-CoA synthase inhibitor;
(c) Squalene epoxidase inhibitor;
(d) Probucol;
(e) Niacin;
(f) Gemfibrozil;
(g) Clofibrate; and
(h) LDL-receptor gene inducer.

* * * * *